(12) United States Patent
Gough et al.

(10) Patent No.: US 8,439,843 B2
(45) Date of Patent: May 14, 2013

(54) AUTOMATIC ANKLE BRACHIAL PRESSURE INDEX SYSTEM

(75) Inventors: Nigel Gough, Pontyclun (GB); Jon Evans, Cardiff (GB)

(73) Assignee: Huntleigh Technology Limited (GB)

( * ) Notice: Subject to any disclaimer, the term of this patent is extended or adjusted under 35 U.S.C. 154(b) by 1220 days.

(21) Appl. No.: 12/280,362

(22) PCT Filed: Feb. 23, 2007

(86) PCT No.: PCT/GB2007/000629
§ 371 (c)(1),
(2), (4) Date: Sep. 4, 2008

(87) PCT Pub. No.: WO2007/096632
PCT Pub. Date: Aug. 30, 2007

(65) Prior Publication Data
US 2009/0036786 A1 Feb. 5, 2009

(30) Foreign Application Priority Data
Feb. 23, 2006 (GB) .................................. 0603564.6

(51) Int. Cl.
*A61B 8/00* (2006.01)
*A61B 8/04* (2006.01)
*A61B 8/06* (2006.01)
*A61B 5/00* (2006.01)
*A61B 5/0295* (2006.01)

(52) U.S. Cl.
USPC ........... 600/481; 600/485; 600/490; 600/492; 600/493; 600/494; 600/495; 600/504; 600/507; 606/201; 606/202

(58) Field of Classification Search .................. 600/481, 600/485, 490, 492, 493, 494, 495, 504, 507; 606/201, 202
See application file for complete search history.

(56) References Cited

U.S. PATENT DOCUMENTS

| | | | |
|---|---|---|---|
| 2,724,129 A | 11/1955 | Pugh | |
| 3,118,440 A | 1/1964 | De Dobbeleer | |
| 3,581,734 A | 6/1971 | Croslin et al. | |
| 3,826,249 A | 7/1974 | Lee et al. | |
| 4,029,087 A | 6/1977 | Dye et al. | |
| 4,210,154 A * | 7/1980 | Klein | 600/498 |
| 4,300,759 A | 11/1981 | Caplan | |
| 4,669,485 A * | 6/1987 | Russell | 600/492 |
| 4,821,734 A | 4/1989 | Koshino | |
| 4,841,956 A | 6/1989 | Gardner et al. | |
| 5,050,613 A | 9/1991 | Newman et al. | |
| 5,496,262 A | 3/1996 | Johnson, Jr. et al. | |
| 5,626,556 A | 5/1997 | Tobler et al. | |
| 6,203,510 B1 | 3/2001 | Takeuchi et al. | |
| 6,378,552 B1 | 4/2002 | Pekar et al. | |
| 6,520,919 B1 | 2/2003 | Nunome et al. | |
| 6,524,257 B2 | 2/2003 | Ogura | |
| 6,533,729 B1 | 3/2003 | Khair et al. | |
| 6,913,575 B2 | 7/2005 | Nishibayashi et al. | |
| 7,846,114 B2 | 12/2010 | Webster et al. | |
| 2001/0037068 A1 * | 11/2001 | Goto et al. | 600/485 |
| 2001/0049476 A1 * | 12/2001 | Forstner | 600/494 |
| 2002/0091328 A1 | 7/2002 | Ogura | |
| 2004/0243008 A1 | 12/2004 | Nishibayashi | |
| 2005/0070828 A1 | 3/2005 | Hampson et al. | |
| 2009/0036786 A1 | 2/2009 | Gough et al. | |
| 2010/0036299 A1 | 2/2010 | Gough | |

FOREIGN PATENT DOCUMENTS

| | | |
|---|---|---|
| EP | 0 388 200 B1 | 9/1990 |
| EP | 1 240 866 A | 9/2002 |
| EP | 1 388 319 A | 2/2004 |
| GB | 0956094 A | 4/1964 |
| GB | 956094 A | 4/1964 |
| WO | WO 98/56331 A1 | 12/1998 |
| WO | 2006/049571 A1 | 5/2006 |
| WO | WO 2006/049571 A1 | 5/2006 |

* cited by examiner

*Primary Examiner* — Stacy B. Chen
(74) *Attorney, Agent, or Firm* — Craig A. Fieschko, Esq.; DeWitt Ross & Stevens S.C.

(57) ABSTRACT

An ABPI measurement system includes two cuffs for each ankle and two cuffs for each arm of a patient. Each cuff has chambers. The four cuffs are applied to each limb (or finger or toe), each chamber is inflated simultaneously to a pressure until a Pneumo Arterial Plethysmography (PAPG) signal related to the arterial flow in the limb is detected at the chambers. The chambers are then simultaneously inflated until the PAPG signals are extinguished in each limb, the inflation of chambers continuing for 10 mmHg to 20 mmHg above that pressure. The chambers are then deflated and the pressure at which the PAPG signal returns in the first chamber is recorded for each limb and this value of the pressure is used to calculate the ABPI. The ABPI is displayed or sent to a remote site.

17 Claims, 4 Drawing Sheets

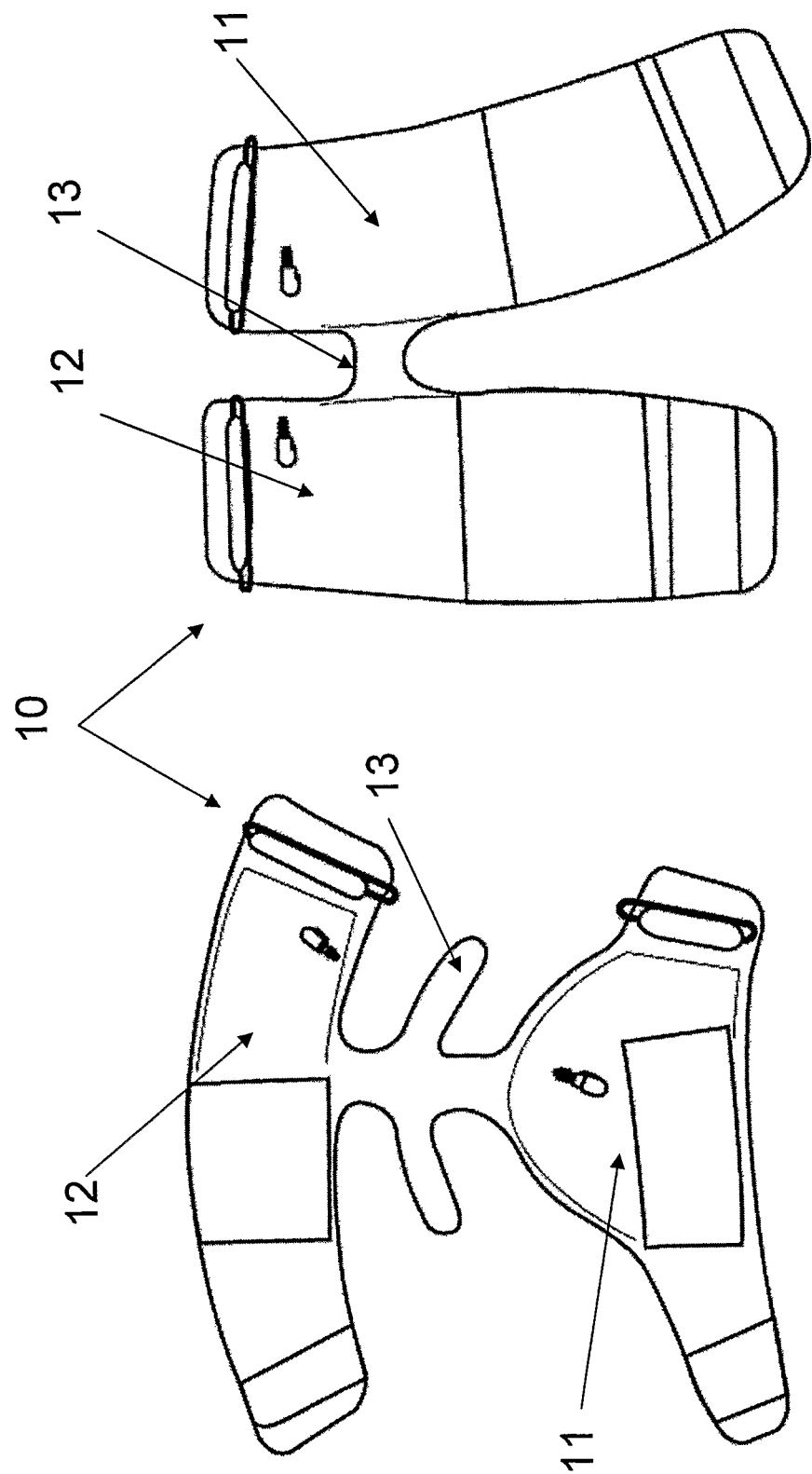

AUTOMATIC ANKLE BRACHIAL PRESSURE INDEX SYSTEM

FIELD OF THE INVENTION

The present invention relates to the identification and assessment of lower limb arterial disease based on an Ankle Brachial Pressure Index (ABPI).

BACKGROUND OF THE INVENTION

ABPI is expressed as the ratio of the ankle blood pressure to the highest brachial (upper arm) blood pressure. Generally, systolic blood pressure values are measured to determine this index. When a certain portion of an artery is affected by occlusive disease, blood pressure downstream of the occlusion in the direction of flow is lower than upstream of the occlusion so that an abnormal ankle and brachial blood pressure index is obtained and arterial disease can be diagnosed.

A known technique to measure ABPI involves the patient being supine and having rested for 5 to 10 minutes. The systolic pressures are then measured sequentially in each of the four limbs by applying a cuff to the upper arms and at the ankles. Usually a hand held Doppler probe is used to listen to the blood flow either in the brachial artery for blood pressure in the arms or in the dorsalis pedis and posterior tibial arteries for ankle blood pressures. However, the technique has difficulties in identifying the arteries in the foot using the Doppler probe as well as maintaining the blood vessel contact with Doppler probe during inflation and deflation of cuff. Also, the blood pressure is continually changing and pressures measured at the beginning of the test may be disassociated with pressures taken at the end of the test.

The use of arterial photo-plethysmography (PPG) can overcome the disadvantages of Doppler. However, it is dependent on the presence of fingers or toes and adequate arterial flow which may be compromised either by temperature or arterial disease. More recently, pulse oximeters have been used for the detection of arterial pulses when taking systolic pressures. However, their use is likely to introduce errors in the pressure readings during deflation of the barometric cuff due to the inherent averaging process within the instrument.

SUMMARY OF THE INVENTION

The present invention seeks to make improvements. Accordingly, the present invention provides an ABPI measuring device comprising a plurality of inflatable cuffs, at least one cuff to be wrapped around an upper limb and at least one cuff to be wrapped around a lower limb, each of the cuffs having a first and a second chamber, means to inflate the first chambers simultaneously to a pre-determined pressure, holding the first chambers at that pressure and inflating simultaneously the second chambers to a desired pressure, recording the pressure and deflating the first and second chambers.

In a preferred embodiment, at least one cuff is wrapped around a finger and at least one cuff is wrapped around a toe, when it is not possible to wrap a cuff around the ankle, for example with a diabetic foot. Preferably, the second chambers are inflated to a pressure greater than the desired pressure and then deflated slowly to the desired pressure.

Preferably, each first chamber is simultaneously inflated to a pressure until a signal related to the arterial flow in the limb is detected. Preferably, each second chamber is simultaneously inflated to a desired pressure until the signal from each first chamber is no longer detected, each second chamber then inflated to a greater pressure than the desired pressure and finally deflated until the signal from each first chamber is detected again and this desired pressure in each second chamber recorded.

Preferably, the device comprises four cuffs, each cuff to be wrapped around each limb or toe or finger.

According to another aspect of the invention, there is provided a method of measuring the ABPI comprising the steps of applying inflatable cuffs to each upper arm or fingers and each ankle or toes of a patient, the cuffs connected to a fluid source and control, each cuff having a first chamber and a second chamber, inflating simultaneously each first chamber of each cuff to a first pressure until a signal relating to the arterial flow in the limb is detected, then simultaneously inflating each second chamber of each cuff to a pressure where the signal is no longer detected, and inflating further the second chambers to a higher pressure, deflating the second chambers slowly until the signal is again detected at the first chamber, the control recording the pressure value of the second chambers, and calculating an ABPI value based on the pressures recorded.

According to an embodiment of the invention, the method of measuring the ABPI comprises applying inflatable cuffs to each upper arm or finger and obtaining pressure values, and repeating the method for each ankle or toe to obtain a pressure value for each ankle and then providing a display of the ABPI. The device has the advantage over the conventional methods of measuring ABPI in that it can make simultaneous measurements of systolic pressures from pairs of limbs, for example, arms or legs or fingers or toes or all four limbs or fingers or toes together. Inflation of pairs of limbs or fingers or toes may be necessary for some patients who are not comfortable with simultaneous inflation of all the limbs or fingers or toes. Inflation of all the limbs or fingers or toes simultaneously obviates the need for a resting period prior to the test.

BRIEF DESCRIPTION OF THE DRAWINGS

Embodiments of the present invention are disclosed below, by way of example only, with reference to the accompanying drawings, in which:

FIG. 2a shows in schematic form the cuff for the arm of the ABPI measurement system according to the invention;

FIG. 2b shows in schematic form the cuff for the ankle of the ABPI measurement system according to the invention;

DETAILED DESCRIPTION OF PREFERRED VERSIONS OF THE INVENTION

Figure 1:
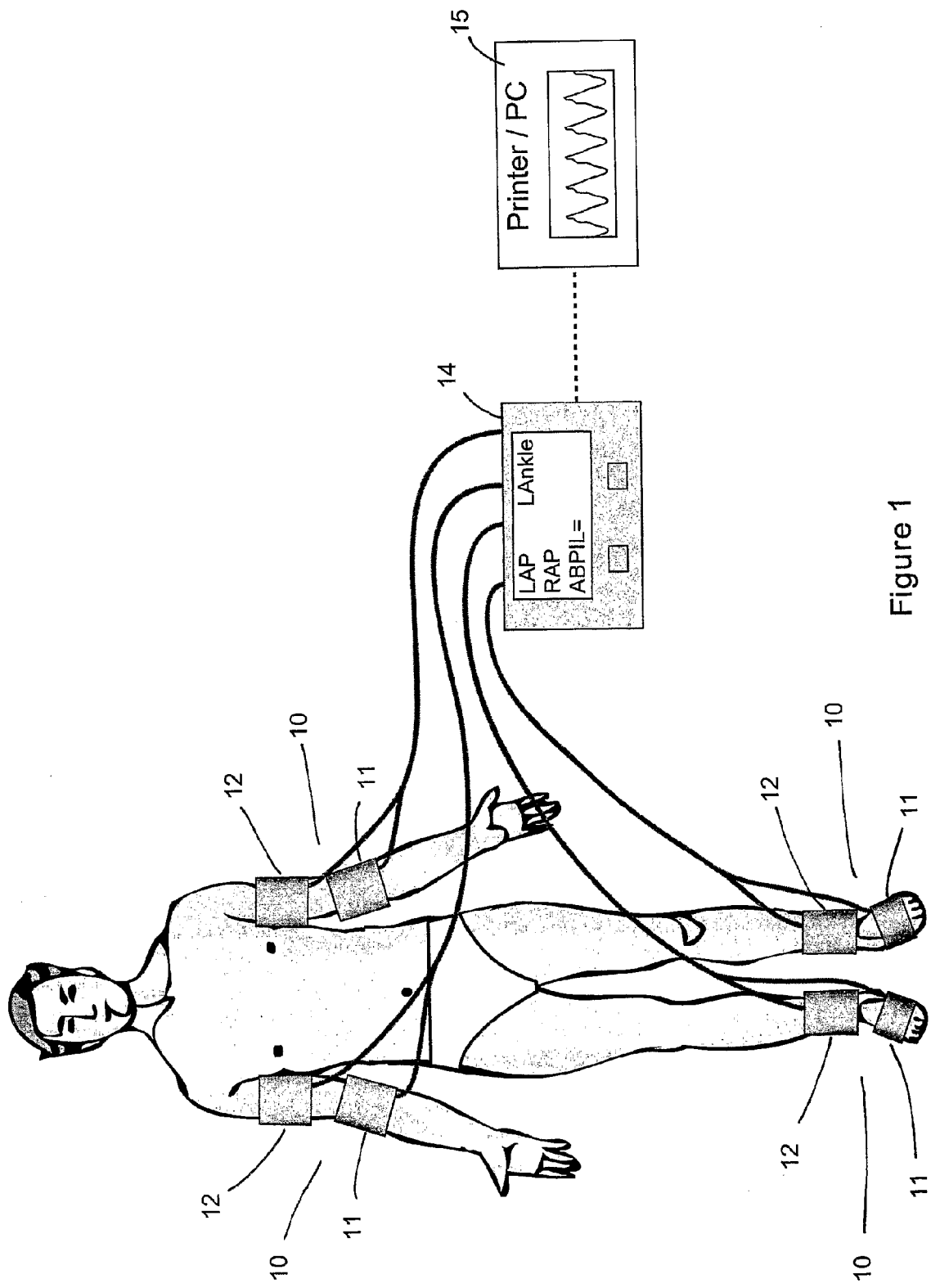
FIG. 1 shows an embodiment of the ABPI measurement system according to the invention.
Figure 2C:
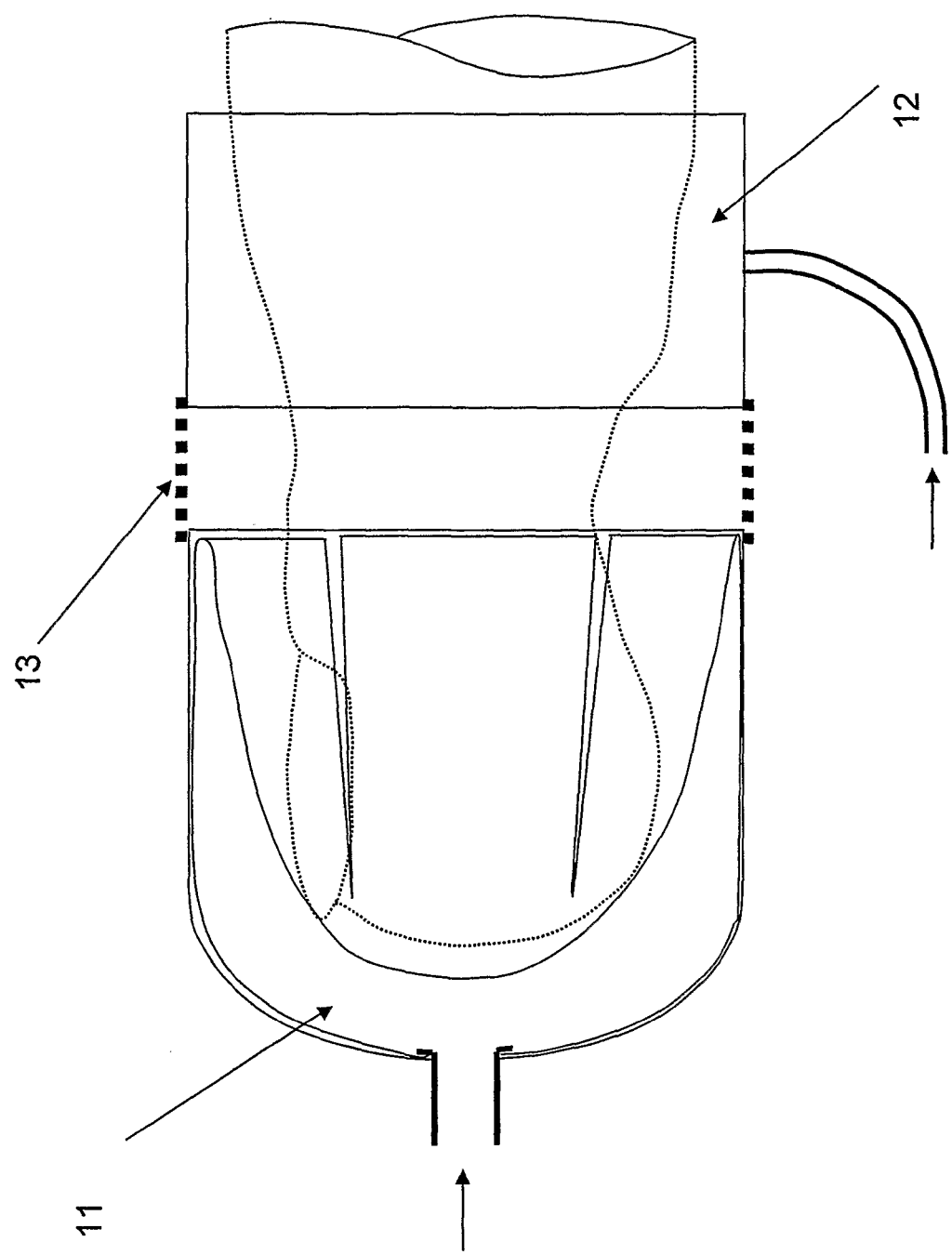
FIG. 2c shows in schematic form the cuff for the toe of the ABPI measurement system according to the invention.

Referring to the Figures, the ABPI measurement system 1 includes two ankle blood pressure measuring devices 10 for each left and right ankle (FIG. 2b) and two arm blood pressure measuring devices 10 for each left and right arm (FIG. 2a) of a patient. As shown in FIG. 2c, it is also envisaged that instead of the two ankle blood pressure measuring devices 10 there could be two toe blood pressure measuring devices and instead of the two arm blood pressure measuring devices 10 there could be two finger blood pressure measuring devices. Each device 10 comprises a cuff having two chambers 11, 12 connected together in a manner so that either chamber does not interfere with the other chamber. The cuff 10 is adapted to be wrapped around the ankle and foot (FIG. 2b) or upper arm and forearm (FIG. 2a) as appropriate.

The chambers 11, 12 are connected by a flexible material 13 such that the action of one chamber does not interfere with the action of the other while maintaining a fixed distance between the chambers and allowing for simple and convenient application to the patient. The chambers 11, 12 are connected to a conventional fluid source for inflation and control 14 having pressure sensors to control the inflation. The fluid source and control are conventional and known to the person skilled in the art and will not be further described herein.

In use, the four blood pressure measuring devices 10 are wrapped around the respective right and left upper and lower limbs of a patient and each chamber 11 is inflated simultaneously to a pressure appropriate for the limb, for example, 60 mmHg for the ankles and arms, and less than 30 mmHg for the toes and fingers, until a Pneumo Arterial Plethysmography (PAPG) signal related to the arterial flow in the limb is detected at the chambers 11. Once a PAPG signal is detected at all four chambers 11, chambers 12 are then inflated until the PAPG signals are extinguished in each limb, the inflation of chambers 12 continuing for a further 10 mmHg to 20 mmHg above that pressure. The chambers 12 are then deflated and the pressure at which the PAPG signal returns is noted for each limb and this value of the pressure is used to calculate the ABPIs according to the equation below, where the highest brachial pressure is the greater value of the left and right brachial pressures;

$$ABPI_{left} = \frac{Ankle\_pressure_{left}}{Highest\_brachial\_pressure}$$

$$ABPI_{right} = \frac{Ankle\_pressure_{right}}{Highest\_brachial\_pressure}$$

$$TBPI_{left} = \frac{Toe\_pressure_{left}}{Highest\_brachial\_pressure}$$

$$TBPI_{right} = \frac{Toe\_pressure_{right}}{Highest\_brachial\_pressure}$$

The system displays the measured systolic pressures and the calculated Left ABPI and Right ABPI. If toe blood pressures are measured then the Left TBPI and Right TBPI is displayed. The ABPI/TBPI value can also be printed as a waveform 15 or communicated to a remote site.

The ABPI/TBPI value is interpreted to give an indication of the status of the arterial system of the patient. Typical results are as shown below:

| | | |
|---|---|---|
| 1) | ABPI >= 1.00 | Normal |
| 2) | ABPI >1.30 | Suspect calcified arteries. Recommend toe pressures. |
| 3) | ABPI 0.8-1.0 | mild PAD. |
| 4) | ABPI 0.5-0.8 | Intermittent claudication. Do not compress. |
| 5) | ABPI <0.5 | Refer to vascular specialist. Do not compress. |
| 6) | TBPI <0.64 | Abnormal indicating PAD |
| 7) | TBPI 0.64-0.7 | Borderline |
| 8) | TBPI >0.7 | Normal |

Figure 3:
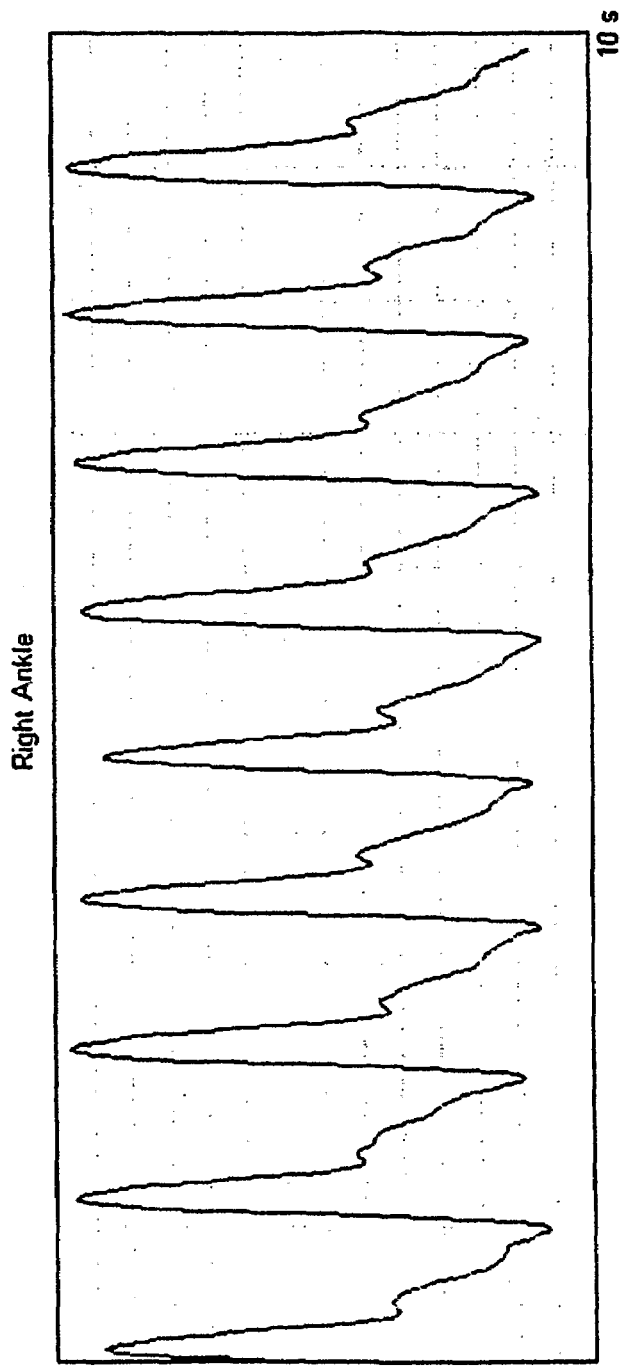
FIG. 3 shows an example of a graph that is displayed on a display device of the ABPI measurement system according to the invention.

Inflation of the chambers 12 to a pressure of 60 mmHg, either before or after the test, allows the system to display the waveforms 15 related to the arterial flow in the limbs as shown in FIG. 3. The waveforms from each chamber 12, can be used for further waveform analysis for the grading of arterial disease.

The above describes a simultaneous four limb blood pressure measurement system. However, it is also possible to stagger the limb pair pressure measurements by taking the arm or finger pressures first followed by the ankle or toe pressures. This may be desirable for patient comfort and clinical safety.

The invention claimed is:

1. A method of measuring ABPI and/or TBPI using at least two inflatable cuffs wherein:
   I. at least one of the cuffs is wrapped around an upper limb,
   II. at least one of the cuffs is wrapped around a lower limb,
   III. each of the cuffs has:
      A. an inflatable distal chamber situated closer to a free end of the limb whereupon the cuff is wrapped, and
      B. an inflatable proximal chamber situated closer to the trunk of a body from which the limb extends,
      the distal and proximal chambers being distanced along the limb;
   the method including the steps of:
   a. simultaneously inflating the distal chambers until the pressures measured therein provide Pneumo Arterial Plethysmography (PAPG) signals;
   b. while the distal chambers are inflated, simultaneously inflating the second proximal chambers until the PAPG signals are no longer detected;
   c. subsequently deflating the proximal chambers until PAPG signals are again detected in the distal chambers;
   d. subsequently deflating the distal chambers.

2. The method of claim 1 wherein:
   a. at least one of the cuffs is wrapped around a finger, and
   b. at least one of the cuffs is wrapped around a toe.

3. The method of claim 1 wherein four inflatable cuffs are provided, and
   a. two of the cuffs are wrapped around upper limbs, and
   b. two of the cuffs are wrapped around lower limbs.

4. The method of claim 1 wherein the proximal chambers are simultaneously inflated to pressures greater than the pressures in the distal chambers.

5. The method of claim 1 further including the step of displaying the pressures of the proximal chambers over time.

6. The method of claim 1 wherein inflation of the proximal chambers continues for a period after the PAPG signals are no longer detected.

7. The method of claim 1 wherein the ratio of the pressures:
   a. in the proximal chamber of the cuff wrapped about the lower limb, and
   b. in the proximal chamber of the cuff wrapped about the lower limb, is calculated, using the pressures in the proximal chambers when the PAPG signals are again detected.

8. The method of claim 1 wherein:
   a. the distal chamber of one of the cuffs, and
   b. the distal chamber of the other of the cuffs, are inflated to different pressures.

9. The method of claim 1 wherein:
   a. the pressures of the distal chambers are measured during inflation of the distal chambers,
   b. inflation of the distal chambers is ceased after the measured pressures of the distal chambers provide Pneumo Arterial Plethysmography (PAPG) signals;
   c. the proximal chambers are thereafter inflated until the PAPG signals are extinguished.

10. The method of claim 9 wherein:
   a. inflation of the proximal chambers continues after the PAPG signals are extinguished;
   b. the proximal chambers are thereafter deflated.

11. The method of claim 10 wherein the proximal chambers are deflated until the PAPG signals return.

12. The method of claim 10 wherein during deflation of the proximal chambers, the pressures of the proximal chambers are recorded when the PAPG signals return.

13. The method of claim 12 further including the step of calculating the ratio of:
   a. the pressure in the distal chamber at the lower limb, to
   b. the pressure in the distal chamber at the upper limb.

14. A method of measuring ABPI and/or TBPI wherein:
   I. an upper limb cuff is wrapped around an upper limb,
   II. a lower limb cuff is wrapped around a lower limb,
   III. each of the cuffs has an inflatable proximal chamber, and an inflatable distal chamber spaced therefrom;
   the method including the steps, for each cuff, of:
   a. inflating the distal chamber to obtain a Pneumo Arterial Plethysmography (PAPG) signal;
   b. while the distal chamber is inflated, inflating the proximal chamber until the PAPG signal disappears;
   c. deflating the proximal chamber;
   d. measuring the pressure in the proximal chamber at which the PAPG signal reappears.

15. The method of claim 14 further including the step of calculating the ratio of the pressures:
   a. in the proximal chamber at the lower limb, and
   b. in the proximal chamber at the upper limb, using the pressures in the proximal chambers when the PAPG signals reappear.

16. The method of claim 14 wherein the steps recited therein are performed first for one of the upper limb cuff and the lower limb cuff, and then for the other of the upper limb cuff and the lower limb cuff.

17. The method of claim 14 wherein the steps recited therein are performed simultaneously for the upper limb cuff and the lower limb cuff.

\* \* \* \* \*